(12) United States Patent
Beekman

(10) Patent No.: US 7,919,756 B2
(45) Date of Patent: Apr. 5, 2011

(54) GAMMA IMAGE DETECTION DEVICE

(75) Inventor: Frederik J. Beekman, Utrecht (NL)

(73) Assignee: Milabs B.V., Utrecht (NL)

( * ) Notice: Subject to any disclaimer, the term of this patent is extended or adjusted under 35 U.S.C. 154(b) by 0 days.

(21) Appl. No.: 12/225,092

(22) PCT Filed: Mar. 14, 2007

(86) PCT No.: PCT/NL2007/000071
§ 371 (c)(1),
(2), (4) Date: Dec. 11, 2008

(87) PCT Pub. No.: WO2007/105942
PCT Pub. Date: Sep. 20, 2007

(65) Prior Publication Data
US 2009/0114825 A1 May 7, 2009

(30) Foreign Application Priority Data

Mar. 15, 2006 (NL) ................................. 1031372
Jan. 30, 2007 (NL) ................................. 1033301

(51) Int. Cl.
*G01T 1/161* (2006.01)
(52) U.S. Cl. ................................. 250/363.02
(58) Field of Classification Search .......... 250/362, 250/363.02; 378/4
See application file for complete search history.

(56) References Cited

U.S. PATENT DOCUMENTS

| 5,525,905 | A  | * | 6/1996 | Mohapatra et al. | 324/318 |
| 6,603,991 | B1 | * | 8/2003 | Karmalawy et al. | 600/411 |
| 2005/0028482 | A1 | * | 2/2005 | Cable et al. | 52/749.1 |
| 2005/0082487 | A1 | * | 4/2005 | Amano | 250/363.03 |
| 2005/0207530 | A1 | * | 9/2005 | Inoue et al. | 378/63 |
| 2005/0213705 | A1 | * | 9/2005 | Hoffman | 378/63 |

FOREIGN PATENT DOCUMENTS

JP 11-190776 A 7/1999

* cited by examiner

*Primary Examiner* — David P Porta
*Assistant Examiner* — Marcus H Taningco
(74) *Attorney, Agent, or Firm* — Birch, Stewart, Kolasch & Birch, LLP

(57) ABSTRACT

The invention provides a detection device and a method of making a gamma detection image.

The detection device comprises a gamma camera and an additional camera, that can make an image of the object outside the gamma detection space. Through correlating the positions of the object with respect to the first and the second camera, the images therefrom may also be correlated.

The correlation of the images allows quick and accurate navigation through the object.

27 Claims, 3 Drawing Sheets

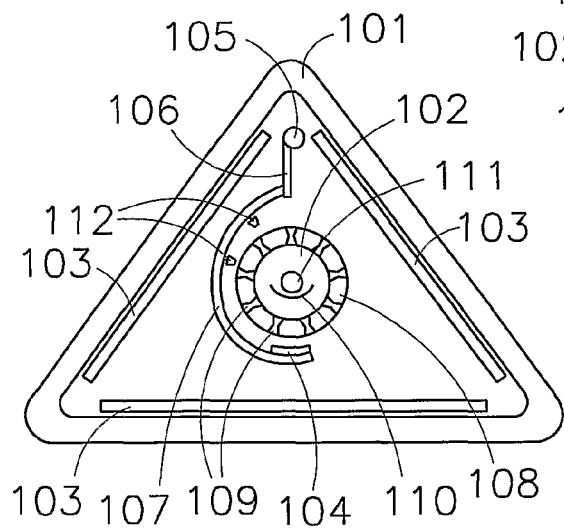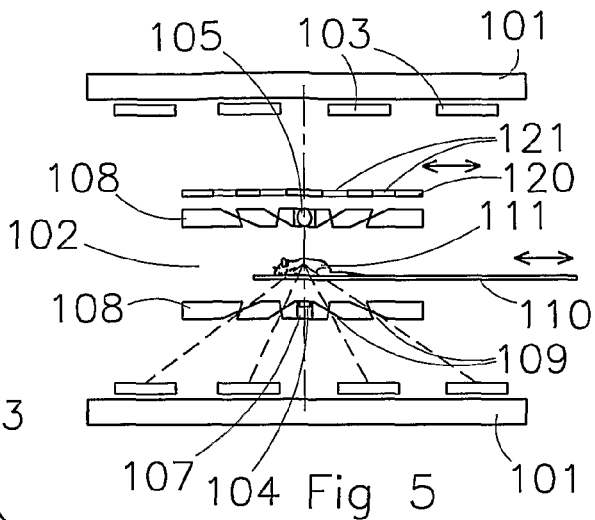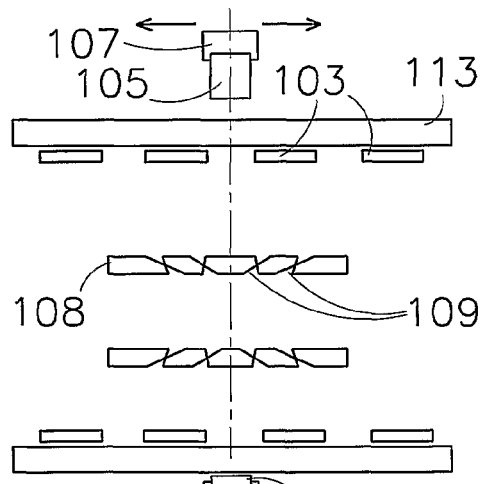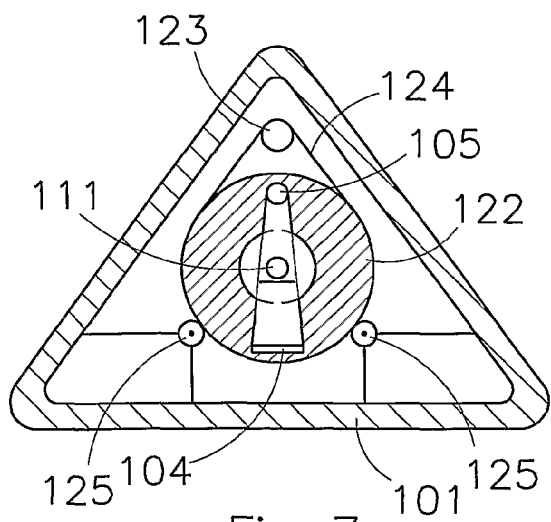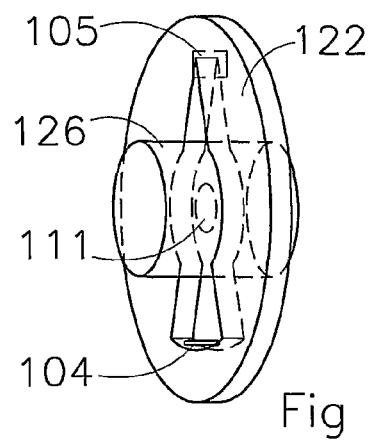

GAMMA IMAGE DETECTION DEVICE

FIELD OF THE INVENTION

The present invention relates to a detection device and a method for making a gamma detection image.

In a first aspect the invention relates to a detection device, comprising a first detector, a second detector, an object holder, an object holder displacement means, and a control device, wherein the first detector comprises a gamma detection space with a gamma camera having a first field-of-view that is located in the gamma detection space, the second detector comprises an additional camera that is sensitive to radiation that substantially differs from gamma radiation, and the control device comprises a screen.

BACKGROUND OF THE INVENTION

Gamma cameras, in particular those which use so called pinholes, often have a (very) long scanning time, due to the relatively low sensitivity of the cameras. This may be unfavourable for the object to be examined, in particular a test animal or human being, since movements during the scanning time have to be prevented as much as possible. This may somewhat be ensured by anaesthetising or by simply not moving. In both cases, this is associated with discomfort for the test animal or human being. Furthermore, in the prior art it is rather common to first position the object to be examined roughly before the gamma camera, in particular if a gamma camera with a small scanning volume is used. After that, a gamma image is formed, on the basis of which it is determined where the scanning volume is located within the object to be examined. Subsequently, the required adjustment in the positioning is carried out. Often, gamma cameras with a high resolution have a small focusing volume, as a result of which "navigating" the focus volume is difficult. This increases the scanning time unnecessarily. In this application, "examining" means collecting data on the object, or part thereof, by means of the gamma camera.

From the article "Detecting Patient Motion in SPECT Imaging Using Stereo Optical Cameras" by Gennert et al., a system is known wherein an image of e.g. a patient is made with gamma cameras, and wherein, at the same time, webcameras make an optical image of the patient. The optical images are used to follow the movement of the patient and to calibrate the images of the gamma camera.

The known system however has the disadvantage that it may not always be used, or at least not well, with many gamma detection systems. This is in particular the case for gamma detection systems with a high resolution that use pinholes positioned close to the object to be examined, and the like. For example, this relates to gamma detection devices in which a test animal is positioned in a narrow tube. In such a case in particular, there is little space for the optical cameras, for these can not be placed in the field of view of the gamma cameras. Also, a good lighting of the object is very difficult in such case.

OBJECT OF THE INVENTION

An object of the present invention is to provide a detection device of the kind mentioned in the preamble, that increases the possibilities to examine an object, and to facilitate navigating through the object when examining with a gamma camera.

SUMMARY OF THE INVENTION

The invention proposes a detection comprising:
a first detector;
a second detector;
an object holder;
an object holder displacement means; and
a control device,
wherein the first detector comprises a gamma detection space with a gamma camera having a first field-of-view that is located in the gamma detection space,
the second detector comprises an additional camera that is substantially sensitive to radiation that differs from gamma radiation, and having a second field-of-view outside the gamma detection space,
the control device comprises a screen, and
the displacement device is arranged to displace the object holder along a path that is controllable by the control device.

In the detection device the image with the gamma camera is still made in the gamma detection space, but an additional image is made with a second detector outside the gamma detection space. Because this additional image is not restricted to the limitations of the gamma detection space, one has, in principle, complete freedom with respect to the additional image and the required equipment.

An advantage is for example that one has more space for making the additional image, and one can also use different detectors, that might be sensitive to gamma radiation. Now, by displacing the object on the object holder over a known path, that may be controlled with the control device, there is still a good spatial correlation between the object's position with respect to the second detector and the object's position with respect to the first detector. Likewise, there is a spatial position correlation between the first image and the second image. In other words, prior to the whole gamma scan, the object to be examined is mapped. Because of that, it is much easier to actually perform the time consuming gamma scan. The device according to the invention is arranged to gather knowledge about the object by means of the additional image, prior to the subsequent gamma detection still to be performed, in order to thereby be able to navigate more easily. This saves precious scan time. The correlation between the second image and the first image, in other words of the second and first field-of-view, may be determined with e.g. a calibration measurement. Thereby it is possible to determine very reliably and accurately a coordinate transform between the object in the first image/the first field-of-view and in the second image/the second field-of-view, by which structures in the object may well be identified and visualized.

In the present invention, "first image" and "second image" only indicate the type of image, and not a temporal order. In fact, the second image, also called additional image, is made before the first image.

Furthermore, "detector", in the expressions "first detector" and "second/additional detector", in each case not only means the actually detecting part but also a detection device as a whole. For example, a first detector is meant to indicate a camera that detects gamma, that thus could itself consist of a plurality of gamma sensitive subdetectors (crystals or the like) with or without a collimator and so on, or also e.g. of one or more gamma sensitive (sub)detectors that are rotated.

An embodiment is characterized in that, in use of the device, the screen is able to display substantially simultaneously a first image of an object made with the first detector and a second image of the object made with the second detector. Herein, it will be clear that the control device that controls the screen is of course arranged correspondingly. With this embodiment, the user is very well able to determine a correlation between e.g. the gamma detection image and the second image such as an optical image.

However, an embodiment comprising a screen and control device that are arranged to display the second image prior to making the first image is particularly advantageous. Herein, the circumstance that the second image can be used to navigate in the object (part) to be examined, that is to say to position the object with respect to the first detector, comes out well, and this without the limitations of a webcam positioned within a gamma camera, according to the prior art. Herein, it is possible to make the first image, the gamma detection image, outside the device, on the basis of the collected data, for example by means of an external image reconstruction computer. Of course, it is preferable if the device, in particular the control device, is arranged to make the gamma detection image, on the basis of the data collected by the gamma camera. Further details and advantageous aspects hereof will be given further below.

In a preferred embodiment the detection device comprises a plurality of additional detectors, i.e. additional cameras. This could be e.g. a plurality of additional detectors or camera of one and the same type, to thus enable a spatial reconstruction. Examples thereof will be given here below. But it could also be different types of additional detectors or cameras, to thus make different kinds of second images.

In a particular embodiment, the additional detector comprises an optical camera, a Magnetic Resonance scanner or an X-ray camera, in particular a transmission X-ray-CT scanner. Such cameras are particularly suited to obtain additional images, that could be used to determine an interesting part of the object to be examined. Advantages of an optical camera are in particular the high resolution, the low cost price, the speed and the ease of interpretation of the images. An X-ray camera offers the advantage that this is also able to look into the object to be examined, and thus enables a comparison with the first image from the gamma camera.

For example in case there are provided a plurality of additional, i.e. second detectors of the same type, it is possible to make a spatial reconstruction of the object. Methods suited thereto are known in the art and will be discussed here below as far as necessary. Of course, other types of additional detectors, such as ultrasonic detectors and so on, could also be used if such provides a desired different image of the object. However, e.g. MRI devices are often very bulky and often even located in a separate room. Thus, these may often not well be combined in the device according to the invention.

In a special embodiment the second field-of-view comprises the complete object to be examined, at least the complete part to be examined of the object. This offers the advantage that the second image provides an overview of the object, or part thereof, to be examined. This enables reliable and accurate navigation through the object, i.e. positioning the object with respect to the first field-of-view. If desired, the second field-of-view may be adjustable, e.g. with a zoom function. Of course, it is not necessary for the second field-of-view to comprise the complete object. In particular with large objects, such as a human being, a much smaller part is also sufficient as a "framework" for measurements with the gamma camera(s). Again, it holds that this is relevant in particular if the field-of-view (or focus volume) of the gamma camera or gamma detector is (much) smaller than the second field-of-view, because navigating can thus be made much easier.

In particular, the control device is arranged to display the first and second image next to each other on the screen. This enables in a very simple way for example to evaluate the first image, such as on the location of tracer uptake in the body, and to determine if a different part of the object, for example located in the vicinity, should also be examined. Such an assessment may take place on the basis of the gamma detection image made. In this embodiment, an pointing device, such as a cursor or a set of lines that can move on screen simultaneously and in a coupled fashion, could be advantageous.

Advantageously, the control device is arranged to project the first image in, or over, the second image, or to project the second image over the first image. Herein, the projection should preferably be brought about such that both images are substantially in register and/or are still at least partly visible, that is to say, the first image is e.g. rendered (partly) transparent. If, for example, the first image is much smaller than the second image, one can display the first image over the second in a "hard" fashion, i.e. opaque. Or one of the first and second image is rendered in a first colour scheme, such as black and white, while the other of the first and second image is rendered in a different colour scheme, such as in natural colours, false colours and so on. This embodiment is particularly suited for interpretation of the images, such as localizing isotope accumulations, and to navigate through the object to be examined, because their spatial coherence emerges very well.

In a special embodiment, the control device is switchable between displaying, i.e. of the first and second image, next to each other and displaying on top of each other. This offers the possibility on the one hand to assess the gamma detection image well in the context of the rest of the object to be examined, while on the other hand, when displaying next to each other, both displayed images are visible optimally. Exactly because the images can be assessed so well, in particular as to their (spatial) context, it is very well possible to control the position of the gamma camera expediently, and in particular already prior to the gamma scan. And so the invention provides the possibility to scan the desired part as specific and fast as possible.

In a particular embodiment, the control device is arranged to project an anatomical image or atlas of at least a part of the object over the first and/or second image. In this case the object will often be a test animal or human being, and the part of the object may e.g. relate to an organ or another specific tissue. An anatomical image or atlas is available for very many animal species and for humans, and comprises a spatial or non-spatial image of one or more organs or organ systems or other division of the body thereof. Here, an anatomical image (or atlas) also comprises that of a representative animal or part thereof, or a separate anatomical or structural image of such an animal or human being. Such an anatomical atlas may have been obtained from a library, i.e. as an average for the specific animal species or man, from a previous image or reconstruction of the animal concerned or a comparable animal, or e.g. on the basis of an image or reconstruction of that animal by means of an image that was made before or elsewhere, e.g. as with an external scanner, such as a Magnetic Resonance scanner or transmission X-ray CT scanner detection device.

Advantageously, the control device is arranged to process at least one of the first and second image and render it as a two-dimensional image, a three-dimensional spatial reconstruction or a cross-section (slice) thereof. With such a rendering, a convenient format of the image(s) is provided, that allows simple, fast and accurate navigation through the object to be examined, and in particular prior to the actual gamma image acquisition (data acquisition). Herein, other ways of rendering the images are not excluded.

In particular a control device that is arranged to display a three-dimensional reconstruction of two or more additional (i.e. second) images offers advantages when navigating, wherein the image thereof on the screen is again a two-dimensional projection or cross-section. For the object may thus be positioned under the angle best suited for assessment or selection, in order to thus select a part to be examined with great accuracy. By the way, it is also possible to provide a plurality of second images on the screen or screens, such as views from different angles.

In particular, the control device is arranged to adapt a rendering of at least one of the first and second image and the anatomical atlas to the rendering of the other of the first and second image and the anatomical atlas. Preferably, this is done such that the first and/or second image and/or the anatomical atlas overlie each other. Thereto, the image may e.g. be scaled up, or down, or in some other way, in one or more dimensions, e.g. by means of a registration technique, in order to bring the images mutually in register. Of course this is connected with the fact that an anatomical atlas relates to an average for the particular animal species or man, while an actual test animal or human being may have other dimensions. Often however, an anatomical atlas provides a fine starting point for the position of organs or other parts to be examined.

It goes without saying with the above embodiment that the rendering of the first and/or second image and/or the anatomical atlas in an overlying fashion is done such that the overlapping parts thereof do actually relate to corresponding parts of the object to be examined. However, it is not necessary that the scales of the images and/or the anatomical atlas are the same. E.g., it is possible to select the scale for the first image (i.e. the gamma image) larger than that for the second image. In that case, an enlargement of a part of the object is displayed. Nevertheless, it is advantageous if the centre of the first image is imaged substantially on the corresponding part of the second image or of the anatomical atlas.

It is remarked here that the strength of the invention partly lies in the fact that image processing and rendition may optimally be made use of, to thus facilitate the navigation and positioning. Per se, many image processing and image rendition techniques are known, the skilled person being able to select the one(s) that work best for him. E.g., he selects a sliced rendition, or a spatial reconstruction, of optical images ("photographs"), MRI images, and so on. A similar series of techniques is available for the first image(s), in other words the gamma detection images, and for anatomical atlases and the like. Through suitable choices there is provided the most convenient rendition for performing the gamma detection expediently, quickly and accurately, and also assessing it with respect to the vicinity of the part to be examined.

In a special embodiment, the displacement device is arranged to displace the object holder in at least two dimensions. Herein, displacing also comprises rotating and the like. Although it is also possible to provide only one-dimensional displacement, displacement in two dimensions of course offers the advantage that the object to be examined may be imaged or examined in a more flexible way or if desired with a higher resolution. Advantageously, the displacement device is arranged to displace the object holder in three dimensions. This provides maximum freedom of movement when examining the object. Such a freedom of movement shows to advantage if the gamma detector has a small field-of-view or focus volume. For then fast and simple navigation is very useful. Often such cameras have a high resolution but also a relatively long scanning time. By being able to delimit the volume to be scanned in advance, the scanning time is reduced strongly.

In particular, the detection device comprises a plurality of gamma cameras. With this is meant that the detection device comprises e.g. a plurality of detectors with a gamma camera, or also one or more detectors with each a plurality of gamma cameras. In fact, a single detector may comprise e.g. a plurality of pinholes. In fact, in this context every device that projects an individual image is considered a gamma camera. E.g., a group of pinholes in a block may thus be considered a group of gamma cameras. Providing a plurality of cameras offers the possibility of a higher resolution, with better noise reduction and/or a higher sensitivity. With a suitable configuration of the plurality of gamma cameras, e.g. around the detection space, it also offers the possibility of making a three-dimensional reconstruction of the object to be examined.

Advantageously, the respective fields-of-view of the cameras overlap only partly, wherein these define a preferential volume. With such a detection device, a high spatial definition and a high resolution may be obtained. This type of detection device in particular often has a relatively small detection space, wherein e.g. pinholes are positioned close to the object to be examined. Herein, "field-of-view" means "field-of-view in the object space", i.e. the part of the object space that is seen by the detector surface, and not the field on the detector surface.

In particular, the control device is arranged to make and display a spatial reconstruction from respective first images of the focus volume of the gamma camera. Such a spatial reconstruction offers advantages when displaying the gamma image to the user, in particular with respect to the second image of the object to be examined. This makes possible a better and quicker navigation through the object to be examined.

In a special embodiment, the control device is arranged for selection by the user of a part to be examined of the object on the object holder. With this is meant that the user selects a to be examined part of the object in e.g. a second image, by means of a mouse or other selection device. In other words, a preferred embodiment comprises a selection device for selecting a part to be examined of the object on the object holder. The selection device e.g. comprises a mouse, drawing pen, touch screen or such pointing device, that is able to select a part to be examined, by means of the second image on the screen, through dragging, drawing or the like. The selection device may also comprise limiting lines that are controllable by the control device. The user may then select a part to be examined by displacing the limiting lines to the limits of that part in the second image. Herein, it may suffice to provide e.g. four controllable limiting lines. By turning, or the like, of the second image, a different view of the object may be obtained. If subsequently the limiting lines are set again, the part to be examined may be limited yet further.

In an embodiment, the device according to the invention comprises a plurality of additional cameras, i.e. second detectors, wherein the control device and the screen are arranged for display of either a plurality of second images of the plurality of additional cameras, or a plurality of views of the object, that are desired projections of a three-dimensional reconstruction of the object based on a plurality of second images. The views are e.g. mutually perpendicular projections, e.g. from above, from the left and right, wherein left and right are often mirror images and thus show a certain form of redundancy. As already indicated above, such a multiple display offers advantages in navigating and/or determining an area to be examined. The number of additional cameras is preferably at least two, to be able to make a spatial reconstruction, although per se a single optical camera that is rotatable around the second field-of-view would suffice. Advantageously, three optical cameras are provided, so that the object may simply be examined from all sides and a reliable feedback can take place, for example to optically "position" a detected tumor on the animal or human. Very advantageously there are even provided four optical cameras on all sides, in a mutually perpendicular fashion, wherein the object holder is transparent. This enables a very simple reconstruction and optical interpretation.

Advantageously, the one or more additional images are stored for later use, e.g. renewed position assessment of additional gamma detections.

Advantageously, the selection device is arranged for selecting a to be examined part of the object in a plurality of second images, in a plurality of views of the object, respectively. Selecting may again be performed by means of a pointing device, with the help of controllable limiting lines for framing, and so on. Because this selection now takes place in a plurality of images or views, a to be examined part may be selected very accurately in three dimensions, which not only increases the accuracy, but in particular also shortens the scanning time.

In an embodiment, the control device is arranged for selecting a part of an anatomical image, in particular an organ, or organ group, a body part or tissue of an animal or human being. Advantageously, the control device and the screen are arranged to display only the selected part of the anatomical image on the screen. A user for example selects the heart of a test animal. The control device then displays not the complete anatomical atlas but only the heart. The user may subsequently use this image to also select the heart in the second image. Advantageously, the control device is arranged to automatically turn a part that is selected in the anatomical atlas into the to be examined part of the object. This offers a very great ease-of-use to the user. For he is often interested in examining an organ or body part. Now, by selecting this part in the anatomical image, and by having the control device designate that part as the part of the object to be examined with a gamma detection, one can very easily and especially very expediently make a gamma detection image.

Advantageously, the detection device is further arranged to displace the object holder in a such a way that, after displacement, the part to be examined overlaps with the focus volume. That is to say, in the case that the part to be examined is small with respect to the focus volume it is of course sufficient if the part to be examined is located in the focus volume, wherein a single image in principle suffices. In the case of a relatively small focus volume, the focus volume will be located in the part to be examined, and may scan the part to be examined, if desired. Very advantageously, the control device is arranged to make a gamma scan of the selected part of the object to be examined by scanning the focus volume through the selected part.

In particular, such a displacement is done automatically, i.e. by the control device, on the basis of coordinates of the selected part to be examined. For then, selecting is nothing more than pointing to a position or volume in the object to be examined, correlated to the position of the object holder with respect to the second detector. Since the focus volume is also located in a known position, in particular a fixed position, it is simple to calculate in which way the object holder must be displaced to position the selected part to be examined in the focus volume. The said displacement may relate to a displacement from a first position, in which the second image is made, to a second position, in which the first (or gamma) image is made, in other words an insertion displacement. Of course, the displacement may also relate to a displacement from a first gamma detection position to a second gamma detection position, in other words a displacement within the gamma camera proper.

This displacing, that is based on second images made in advance, strongly reduces the scanning time, and furthermore strongly increases the convenience for both the user and the object to be examined. One of the biggest advantages of this navigating, in particular in gamma cameras with a relatively small focus volume, is that prior to the gamma scan(s) the desired gamma detection position may be determined by means of the second image. In an exemplary embodiment the gamma camera comprises a camera of the U-SPECT type. For constructional details thereof, reference is made e.g. to the article 'U-SPECT-I: A novel system for submillimeter-resolution tomography with radiolabeled molecules in mice', by F. J. Beekman et al., J. Nucl. Med., Vol. 47, No. 7 (2005). These cameras have a high resolution but a relatively small focus volume. In such camera, the advantages of the invention show well.

The invention further relates to a method of making a gamma detection image, using a detection device according to the invention, comprising the steps of a) positioning an object on the object holder, b) making and displaying a second image with an additional detector, c) selecting a part of the object to be examined, d) determining a path along which the object is to be displaced, and e) making and displaying a first image, being the gamma detection image. With this method, a gamma detection image of an object to be examined, or a desired part thereof, may be made in a fast and expedient way. Correlating, in particular bringing in register, of the second image and the first image (gamma detection image) is very easy and very accurate. Thereto, for example a calibration measurement is carried out with known gamma point sources that are also visible optically (fiducial markers), so that the spatial transform for a displacement is known, and may be calculated for other displacements based on reconstruction techniques and marker positions known per se. Herein, the path serves to displace the object in such a way that, after displacement, the selected part to be examined is located in the field-of-view, or the focus volume, of the gamma camera.

Advantageously, the second image is displayed on the screen first. On the basis thereof, a part to be examined may then be selected, as also in the description of the device according to the invention, after which a gamma detection image of that part is actually produced.

In particular, the first and second image are displayed on the screen simultaneously. Herein, one may e.g. choose to display the first and the second image next to each other or over one another. Of course, this can only take place after the first image has been made. Again, it holds that this should be done in such a way that relevant parts of the first and second image are still visible, such as different colour schemes, partly transparent rendering, and so on. It is also possible to display an anatomical image or atlas of (the part of) the object to be examined.

Advantageously, at least one of the first and second image are displayed as a two-dimensional image, a three-dimensional spatial reconstruction or a cross-section (slice) thereof. Such displaying may e.g. be done as a two-dimensional projection of that spatial reconstruction, or a view under a desired angle. Very advantageously, the first image is projected into the second image. This provides a good overview of the mutual position of the first field-of-view in the second image, and makes expedient navigation therein very simple. Of course it is also possible to display the non-processed first and second image, and if desired next to each other instead of over one another. Further, all above remarks also hold for a possibly displayed anatomical atlas and the like.

Preferably, the anatomical image or atlas is brought in register with the second image. Here, as in all of the text, "bringing in register" means that the images are scaled in one or more dimensions such that corresponding dimensions and structures are displayed the same as much as possible, i.e. both as to their proportions and as to their absolute dimensions. Other terms therefor are "to draw in/to plot" or "to cause to overlap". E.g., it relates to an anatomical atlas that is imaged onto, or better in, a second image such as an optical image of the object. Then, it becomes easy to select in the object, by means of a pointing device such as a mouse or touch screen, an area to be examined, such as a heart, a tumor with surrounding area, or brain area, in the case of a test animal or human being. This can be done in a two-dimensional image, but preferably in a three-dimensional image of the object. Thereto, for example a 3D reconstruction is made, based on the second image(s), after which the anatomical atlas is brought in register therewith. Thus, a 3D framework is provided to navigate the (subsequent) gamma detection in the object. Here, it is stressed again that the terms "second" and "first" only serve as a reference, not as an indication of a time order, since the second image is in principle made before the first.

In an embodiment, display of the second image is ended. In this way, only the anatomical image or atlas is displayed, and only the most relevant part of the object is displayed, such as the skeleton, the heart and so on. If, subsequently, the first image is displayed, either next to it, or within it/on top of it, then the context, the spatial connection and so on, may be recognized most clearly. In particular, the method comprises the step of selecting a part of the anatomical image as the to be examined part of the object. Advantageously, the control device then only displays the selected part of the anatomical atlas on the screen. This provides a very good impression of, and help in navigating in, the object to be examined within its spatial context.

Preferably, determining of the path takes place by the control device automatically, after a user has selected a part of the object to be examined. Advantageously, the steps c) through e) are repeated. Again, it holds here that, if a user selects a part of the object to be examined, there arises a correlation between the coordinates of the particular part and the object holder, which may be coupled to the field-of-view of the gamma camera in a known way. The displacement concerned of the object holder can easily be calculated and carried out. In this way, a gamma detection image may be formed quickly and accurately. Herein, it holds that determining the path relates to both the displacement of second field-of-view to the first field-of-view, and a possible displacement within the first field-of-view, such as a scanning displacement. This latter displacement may e.g. be necessary if the focus volume of the detection device used is smaller than the volume of the part to be examined.

Here, it is remarked that the control device may comprise a computer or similar circuits, for carrying out the various steps described. The screen too may comprise any known type of display, such as a TV, a phosphorescent screen (with afterglow), and so on, but also by means of computer graphics. The object holder displacement means may of course be controlled by the control device, and may comprise any known type of displacement means, such as electromotors, piezoelectrical motors, and so on.

The present invention, in a further aspect, also relates to a multimode detection device, comprising a frame with a central detection space, a gamma detection device, having at least one gamma camera with a gamma radiation sensitive gamma detector surface, wherein the gamma camera comprises a SPECT scanner, with a collimator, and a transmission CT scanner (TCT scanner) with a radiation source for emitting transmissive radiation, and a transmissive radiation sensitive TCT radiation detector surface, which gamma detection device and transmission CT scanner are arranged to form an image of at least a part of the object in the detection space by means of the gamma radiation, the transmissive radiation, respectively.

Such detection devices are known. E.g., document U.S. Pat. No. 6,399,951 describes a system for simultaneous X-ray CT -and SPECT tomography. The system comprises a gantry with an X-ray source and an X-ray detector, wherein the object to be examined may be positioned in a detection space in the bore of the gantry. In use, the X-ray source revolves around the object, while simultaneously the detector co-revolves on the opposite side of the object. In this way, a transmissive X-ray image can be obtained. Furthermore, the detector is able to detect gamma radiation emitted by that object, as a result of which in the same way an emissive gamma image may be obtained. A disadvantage of the known device is that this has a relatively low sensitivity and resolution, in particular for the gamma image, indicated in the document as about 5 mm. Furthermore, the known device is not particularly flexible or user-friendly.

An object of this aspect of the present invention is to provide a detection device of the indicated kind, that is more flexible in use and/or has a higher resolution, in particular for the gamma camera.

At least a part of the above objects are achieved with a multimode detector device according tot claim 30. Partly due to the gamma detector surface extending around the detection space, and not being only the same as the TCT radiation detector surface as in the known device, and to the gamma camera of the device comprising a collimator, a significant improvement in sensitivity and resolution can be achieved. Herein, it is also an advantage that the gamma detector surface extends on both sides of the TCT radiation detector surface, in other words that the TCT radiation detector surface is located between the boundaries of the gamma detector surface, as seen in the longitudinal direction of the detection space. Due to this, it is possible to yet make a gamma image and a TCT radiation image substantially simultaneously. Herein, "simultaneously" means that the object need not be displaced.

It is remarked here that multimode detection devices that are a combination of a gamma camera and an X-ray CT scanner, wherein the gamma detector surface extends around a detection space, are known in the prior art. For example, U.S. Pat. No. 6,961,606 discloses such a device. However, here, the two detection subdevices, such as a CT scanner and a PET scanner, are positioned behind each other. This has the disadvantage that the object must be displaced, which may introduce undesired artefacts of displacement. In the present invention, this is not necessary, and the device according to the invention is extraordinarily compact, because the transmission CT scanner may be incorporated in the gamma camera. Furthermore, the displacement stroke of the bed, or in general the object holder, can be smaller. For only the stroke required for the CT scanner has to be made, without a displacement from the CT scanner to the gamma camera or vice versa.

In the context of this aspect of the invention, we speak of an "object" that may be examined. Herein, sometimes this object is also called "voorwerp" (Dutch for "object"), and may comprise, apart from lifeless objects, also livestock, such as a test animal or human being, in particular a patient.

Furthermore, a characterizing aspect of the device according to to the invention is that it comprises a collimator. Although this may often decrease the absolute sensitivity, through the presence of pinholes, it is possible to take a number of measures that cause a possible loss of sensitivity to be at least partly compensated, and the resolution is often much higher. In a number of cases the collimator "could be in the way". However, this aspect of the invention offers advantageous measures for this, too.

Advantageous embodiments are described in the dependent claims 31-46.

In particular, the transmissive radiation comprises X-rays and the transmission CT scanner comprises an X-ray CT scanner and an X-ray source. Alternatively or additionally, the transmissive radiation comprises gamma radiation and the transmissive CT scanner comprises a gamma CT scanner and a gamma source. Incidentally, in the present document, "transmissive CT scanner" is sometimes abbreviated to TCT scanner. The said types of transmissive radiation with corresponding CT scanner and radiation source are suitable because of the availability of relatively compact sources, but are not limiting. Alternative transmissive radiation is e.g. synchrotron radiation. Advantageously, the spectrum of the gamma radiation of the gamma source differs from that of the gamma radiation of the gamma tracers to be brought into the object. This not only makes it possible to distinguish between the gamma images, but it may also be advantageous due to the different penetration level for particular parts of the device, whether or not optional, such as in particular the edges of pinholes. Note that the gamma camera(s) form an emissive scanning device, which thus records radiation that is emitted by sources within the object to be examined, in this case mostly gamma tracers.

In an advantageous embodiment, the gamma detector surface comprises the detector surface that is sensitive to the transmissive radiation. In other words, the gamma sensitive surface of (at least a part of) the gamma camera(s) is also used as a surface to receive the transmissive radiation from the radiation source of the TCT scanner. This may be the case for e.g. X-rays but also for gamma radiation as the transmissive radiation. Herein, the gamma detector surface belongs thus to the gamma camera, and may also be designated a first detector surface, while the detector surface that is sensitive to the transmissive radiation substantially belongs to the TCT scanner, and may be designated a second detector surface. The first detector surface comprises, in the special embodiment described here, substantially the second detector surface.

An important remark here is that U.S. Pat. No. 6,399,951 per se also discloses that the X-ray sensitive surface and the gamma sensitive surface are one and the same surface, but in this document that is only the revolving detector surface. In the present invention, it is rather the large and stationary surface, viz. the gamma detector surface. For the total sensitivity it is much more favourable to take the complete surface. For there is always a part of the gamma detector surface opposite the revolving source, while for the emissive gamma image to be made simultaneously, a much larger surface is constantly available.

Incidentally, the gamma detection device according to this aspect of the invention advantageously comprises a plurality of gamma cameras, preferably arranged around a detection space.

In an embodiment, the gamma camera comprises a PET scanner with a plurality of gamma detector surfaces, wherein at least two of the gamma detector surfaces may be read out in coincidence mode. Even when using a collimator, a sufficient sensitivity may be obtained. For example, a large number of pinholes may be provided, with a relatively large opening, and advantageously with a large opening angle, that compensates the penetrating power of positron radiation, for example in comparison to that of gamma radiation of about 100 keV that is common for gamma tracers.

The gamma camera comprises a SPECT scanner with a collimator. Herein, the device may comprise a revolving and relatively small gamma detector surface, but in the present invention the detector surface extends around the detection space. Incidentally, both for the SPECT scanner and for the PET scanner, this means that the gamma detector surface may extend continuously in a circumferential direction, but it is also possible that it is built up of a number of parts and extends around the detection space over an angle of e.g. 90°, 180°, or even 360°.

The detection space in most cases has a direction along which an object may be inserted, which direction is designated here as the longitudinal direction. It is often, but not necessarily, an axis of (rotational) symmetry of the detection space. Furthermore, the longitudinal direction is often designated the z-direction, in particular in respect of CT scans, in which a steplike or uniform displacement of the object at least along the z-axis takes place during the CT scan. The detection space may be cylindrical, or e.g. have a tri-or polygonal cross-section. The gamma detector surface too can be cylindrical, or preferably, as a whole, be of a (regularly) tri-or polygonal cross-section. The gamma detector surface may also extend over, in each case, only a part of the faces of a shape with a tri-or polygonal cross-section (profile), and also over parts of a cylindrical shape. For example, the gamma detector surface may be built up of detector subsurfaces.

As mentioned above, the gamma camera, and in particular the SPECT scanner, comprises a collimator, that can increase the resolution. Advantageously, the one or more gamma detector surfaces can be read out in single photon emission mode and/or at least two thereof in coincidence mode, which provides a flexible device.

Advantageously, the collimator is arranged to be shifted in between the gamma detector surface and the object in the detection space, and out again. In other words, the collimator is arranged to be shiftable between the gamma detector surface and the object, which will then be positioned in the detection space. Due to this, the gamma camera may be switchable between PET and SPECT mode, provided the read out of the gamma detector surface is also adaptable correspondingly. For the PET mode, such a configuration, without a collimator shifted in between, may be favourable for the absolute sensitivity.

In an advantageous embodiment, the SPECT scanner comprises a collimator with a plurality of pinholes. In particular, these pinholes are directed such that their main transmission directions converge to a focus volume, preferably to a focal point. Such a focussing SPECT scanner has a very high resolution and sensitivity. Reference is made to, among others, scanners of the U-SPECT-I, II and III of the applicant, see e.g. Design and simulation of a high-resolution stationary SPECT system for small animals, by F J Beekman and B Vastenhouw, Phys. Med. Biol. 49 (2004) 4579-4592. Preferably, the focus volume is located in the centre of he collimator. However, this is not necessary, since an eccentric position of that focus volume, in particular with respect to a rotational axis of the TCT scanner, can also provide useful results. In that way, it is possible e.g. to generate a larger field-of-view, albeit with an adjusted mathematical processing of the results. Advantageously, the collimator is substantially mirror-symmetrical in a plane perpendicular to the longitudinal direction of the detection space. Thus, information about the spatial distribution of the gamma source in the object may be obtained under many different angles. This allows a good spatial reconstruction of that distribution.

Preferably, the TCT scanner extends in said perpendicular plane. With this is meant that a main direction of acquisition extends in said plane, such that a line from e.g. the centre of the source of transmissive radiation to the corresponding detector is substantially in that plane. This is a particularly advantageous embodiment, in which the TCT radiation source and/or the TCT radiation detector surface may also be provided mirror symmetrically with respect to said perpendicular plane. Indeed one or more pinholes may be screened by the TCT scanner, or may even not be provided, but in practice the angular information obtained by the gamma camera turns out to be more than enough to maintain a resolution and freedom of distortion that is almost as good as in the case without screening part of the pinholes. Furthermore, the advantage of simultaneously imaging the object with gamma radiation and transmissive radiation such as X-rays, without displacing same, thus comes out well.

In an embodiment, the collimator comprises at least two collimator parts, wherein, preferably, each collimator part extends on one side of the TCT scanner, as seen in the longitudinal direction of the detection space, and preferably extends at least for the largest part on one side of the TCT scanner. In this embodiment, the collimator is divided into at least two, and preferably two, collimator parts, that extend to the left and right with respect to the TCT scanner, preferably but not necessarily in a symmetrical fashion.

Advantageously, the collimator parts are displaceable with respect to each other between a first position, in which they form a contiguous collimator, such as a collimator cylinder or a regular collimator polygon (at least in cross-section), and a second position, in which, as seen in the longitudinal direction of the detection space, there is at least one collimator part on both sides of the TCT scanner. Herein, the TCT scanner is located between the collimator parts, with a free field-of-view. In this way, optimum use may be made of the flexibility of the device. If only a gamma scan needs to be made, the collimator parts may be abutted into e.g. a collimator cylinder or regular collimator polygon. If a CT scan has to be made, the collimator parts may be moved apart and the TCT scanner can do its job by moving the collimator parts apart. Note that, in many cases, a CT scan can be made much faster than a SPECT scan. In a combination of CT and SPECT hence relatively little time is lost as compared to a normal pure SPECT scan.

In an embodiment, the gamma detector surface comprises at least two gamma detector surface parts. In a special embodiment, each gamma detector surface part extends, as seen in the longitudinal direction of the detection space, on one side of the TCT scanner.

Advantageously, the gamma detector surface parts are displaceable with respect to one another between a first position in which they form a contiguous cylindrical or regularly polygonal gamma detector surface, and a second, moved apart position, wherein, advantageously, on each side of the TCT scanner, as seen in the longitudinal direction of the detection space, there is at least one gamma detector surface part. In this embodiment, the gamma detection device splits up in two, as it were, wherein room is made for the TCT scanner, e.g. in order to revolve around the object to be examined in a somewhat larger distance. In particular in combination with the collimator that can be moved apart, a flexibly applicable device is thus provided.

In the above embodiments, as well as in the embodiments to be mentioned below, the object holder, provided as is usual, may be displaceable at least in the longitudinal direction of the detection space, and advantageously also in one or two directions perpendicular thereto. In particular if there is a relatively small focus volume, a complete scan of the object may still be made by moving the object.

In embodiments, the TCT scanner is arranged on a part that is rotatable around the detection space, and which preferably comprises a ring, a disc or a regular polygon. In this way, known per se, the possibility for a scan all around is provided. If, furthermore, one moves the object on an object holder, a CT scan arises, either stepwise for circular acquisition, or uniform, for a helical scan. Very advantageously, the one or more collimator parts, if provided, are arranged fixedly, which excludes artefacts of displacement during acquisition.

Such a CT scan may often be carried out very quickly. Then it is also possible to select a TCT scanner with a small field-of-view, such that, in that CT scan, there is only a limited volume with complete angular information. By subsequently moving the object in two, and preferably three, directions through that volume, as a whole a total CT-scan of the object may be made, but with the advantages of such a "concentrated", focused CT scan. Of course, this scanning also applies to acquisition with the gamma camera with a focusing collimator.

Advantageously, the rotatable part comprises one or more pinholes, advantageously directed towards the focus volume. This offers the advantage that a relatively large portion of the rotatable part can still form a part of the collimator, and can thus contribute additional angular information to the gamma image. Partly due to the CT scan often taking much less time than a gamma scan, not using those extra pinholes during rotating the rotatable part will not outweigh that additional information. In fact, one big, and more or less contiguous collimator is thus formed, a small part whereof can serve as a TCT scanner.

Advantageously, the device comprises at least one optical camera directed towards the focus volume, more advantageously arranged on the rotatable part. In an advantageous way, with one or more of such optical camera, an additional optical image may be made, or one may even perform optical tomography, in a way known per se. Thereby, images and structures therein, as determined with the gamma scan and/or CT scan, may be localized even more efficiently within the object, often a test animal or human being. Optical information is of course the easiest to access, although it is bound to the outermost layers of the object. Optical radiation may either reflect off the surface and thus provide information thereabout, or it may originate from optical tracers that have been brought into the object. Those optical tracers may then emit light from within, and thus provide information about underlying structures, albeit that the yield for larger depths will decrease quickly. Nevertheless, when using (infra) red light, a useful yield is possible. Furthermore, here too, it is advantageous that these optical images and/or tomography may be made "simultaneously", i.e. without displacing the object. Thus, advanced mathematical calculations are not needed to be able to couple the various types of images with one another.

In embodiments, the distance from the TCT radiation source to the rotational axis is adjustable. The TCT radiation source is in particular displaceable between on the one hand a position outside the collimator, and more in particular into a corner part of a polygonal gamma detector surface, and on the other hand a position within a circumferential surface of the collimator. More generally speaking, the TCT radiation source is displaceable between a kind of "parking position" and a "working position". In the parking position, the distance to the rotational axis is larger than in the working position, in order to be able to obtain a higher intensity in the latter. If the gamma detector surface extends as if on a polygon around the detection space, it is furthermore advantageous if the parking position extends in a corner part of that polygon. Often, in an extreme tip thereof, no gamma sensitive surface is provided, while furthermore, because of the small yield and high distortion, omitting such a (tip) part of the gamma detector surface that is screened by the TCT radiation source hardly affects the performance of the device.

In special embodiments, the collimator comprises a pinhole blocking device, in particular a part that is positioned outside the collimator, for blocking one or more pinholes, wherein this part is displaceable between a first position, in which the holes in said part release the one or more pinholes, and a second position, in which the holes block the one or more pinholes. With such a pinhole blocking device, the gamma detector may be protected against the often much higher intensity, in particular of the X-rays. During a CT scan, the pinholes are blocked if desired, by blocking them by means of the pinhole blocking device, while they are open again during the gamma scan. In case use is made of the embodiment in which the gamma detector surface comprises the surface that is sensitive to transmissive radiation, and if it happens to be that the intensity of that transmissive radiation is much higher than can be handled by gamma detector surface, instead of a pinhole blocking device use may be made of a radiation attenuation device, comprising an attenuator part with sufficient transmissivity for the transmissive radiation, e.g. in the form of an insertable tube, or a kind of pinhole blocking device of an attenuating material instead of a blocking material.

When using a pinhole blocking device, it is still possible to make a gamma image and an X-ray image "simultaneously", if "simultaneously" is interpreted as "without displacement", as indicated above. Alternatively, one can also say that the gamma image is acquired during a much longer time span than the X-ray image, so that this latter may be done partly before, and partly after acquiring the X-ray image. This, too, could be called "simultaneously".

In particular, the pinhole blocking device comprises a part, more in particular a cylinder, cylinder part, sheet or polygon, which part comprises one or more holes that are capable of being brought in register with the one or more pinholes. In use, it is e.g. possible to position the part in an "open" position around the pinholes, such that a gamma scan is possible. If the part has to block the pinholes, it is displaced over only a small distance, in theory the width of a pinhole. Therefore, it may be done very quickly, almost without time delay. The pinhole blocking device is made of a material that sufficiently blocks X-rays or other transmissive radiation, such as a metal sheet. In theory, the pinhole blocking device could even be a closed body without holes, wherein the transmissivity for the transmissive radiation is much smaller than for gamma radiation.

If desired, the part may be connected to, or may even be the same as, a framing device such as a framing tube or framing plate. Such a framing device may be provided in the device in order to define the fields-of-view of the pinholes onto the gamma detector surface. The combination of framing device and pinhole blocking device then has the advantage that fewer parts are required. However, a framing device is often positioned at a different, larger distance from the pinholes, and the framing device is made of a material that is little transmissive to gamma radiation.

Advantageously, the radiation source and the radiation detector surface are integral with at least a collimator, in particular with one of the collimator parts thereof, and/or with one or more framing sheets or framing tubes positioned between the collimator and the gamma detector surface. An advantage thereof is that fewer individual moveable parts are required, so that mutual calibration is easier, and less deviation or displacement in time will take place.

In the following, the aspects of the invention will be elucidated further, with reference to the drawings.

BRIEF DESCRIPTION OF THE DRAWINGS

FIG. 4 shows a diagrammatic cross-section of an embodiment of the device according to a further aspect of the invention;

FIG. 5 shows a cross-sectional side elevational view of an embodiment of the device according to that further aspect of the invention;

FIG. 6 diagrammatically shows an alternative embodiment, in cross-section;

FIG. 7 shows a diagrammatic, cross-sectional side elevational view of an embodiment of the central part of the device according to the further aspect of the invention, with the X-ray CT scanner; and FIG. 8 shows a perspective side elevational view of the embodiment according to FIG. 7.

DETAILED DESCRIPTION OF PREFERRED EMBODIMENTS

Figure 1:
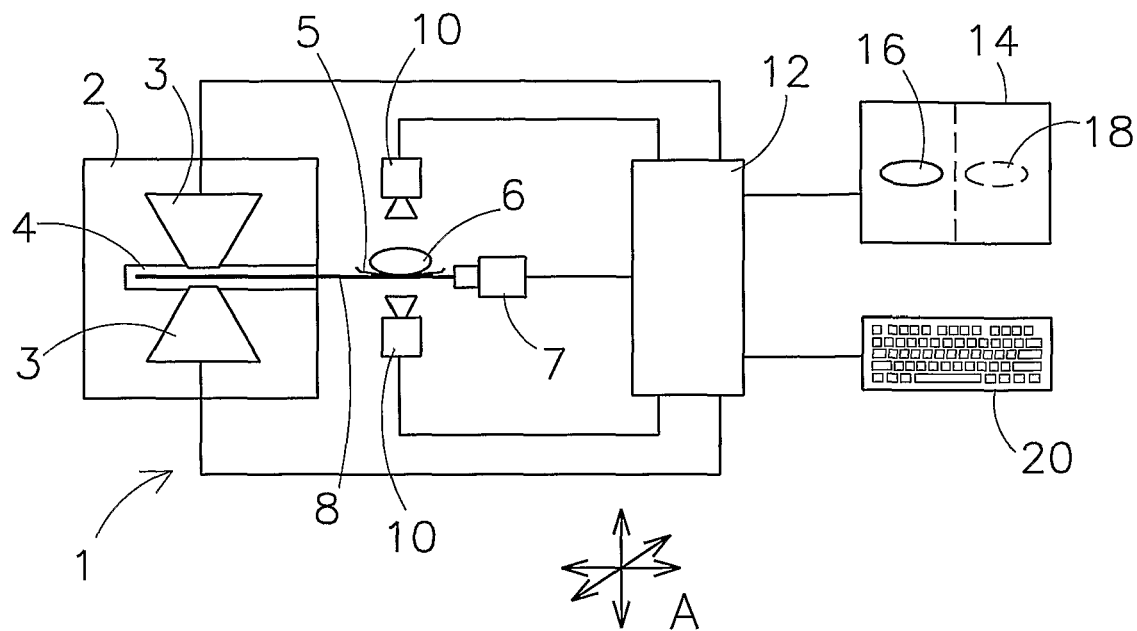
FIG. 1 diagrammatically depicts a gamma detection device.

FIG. 1 diagrammatically depicts a gamma detection device 1. This comprises a first or gamma detector 2 with two gamma cameras 3 and a gamma detection space 4. In it, there is a guide 8, along which an object holder 5 with an object 6 can be displaced by an object holder displacement means 7.

Additional cameras are designated by 10. Furthermore, a control device 12 is connected to a screen 14 for displaying a first image 16 and a second image 18, as well as to a keyboard 20.

The gamma detector 20 here has two gamma cameras 3. Of course, this could also be a single gamma camera. Preferably, there are even three, arranged in a triangle, since this allows a fine recording all around, with good 3D reconstruction possibilities, and yet with a simple configuration. Incidentally, it is remarked here that in this context, gamma camera means both a simple imaging device such as a pinhole camera, and a group of mutually associated imaging devices.

The object holder 5 may e.g. comprise a bed, for example if the object to be examined is a human or a larger test animal. It may also be a dish or even a tube, with relatively small dimensions. For example, it may be a tube with dimensions just big enough to accommodate a mouse. Of course, this tube may be partly cut away, for breathing and general access to the mouse.

Incidentally, the guide 8 is optional, since the object holder displacement means 7 could also fulfil the function thereof, e.g. by means of one or more rods connected to the object holder 5. The object holder displacement means may comprise one or more actuators, such as an electromotor, a pneumatic or hydraulic motor, a piezo-electrical motor, and so on, and it is able to displace the object holder in one or more directions, designated by the crossed axes A.

Here, the additional cameras 10 are two optical cameras. It may also concern a single camera, or even three or more cameras for an optimum spatial image. Furthermore, there may also be provided a different type of camera, alternatively or additionally, such as an infrared camera, a CT scanner or an X-ray camera. For these cameras, too, it holds that there may be one or more. Furthermore, for possible anatomical atlases it also holds that there may be provided more than one, if desired of different types.

Both the one or more gamma cameras 3 and the object holder displacement means 7 and the cameras 10 are connected to the control device, here integrated into one device 12. In most cases, such a control device comprises a computer or similar equipment. Apart from control functions, the computer 12 will often also comprise image processing capability and, if desired, other algorithms, such as image reconstruction algorithms. Such functions may also be provided in separate devices.

The computer 12 is connected to a keyboard 20, which is optional, and it may also be replaced by or supplemented with other input devices, such as a mouse, a disk drive, or an Internet connection.

The screen 14 as shown here displays a first image 16 and a second image 18 side by side. The first image 16 e.g. originates from a gamma detector 3, and the second image from the optical camera 10. Here, they are displayed side by side, but they may also be displayed on top of each other. Below, this will be elucidated further.

Figures 2A, 2B:
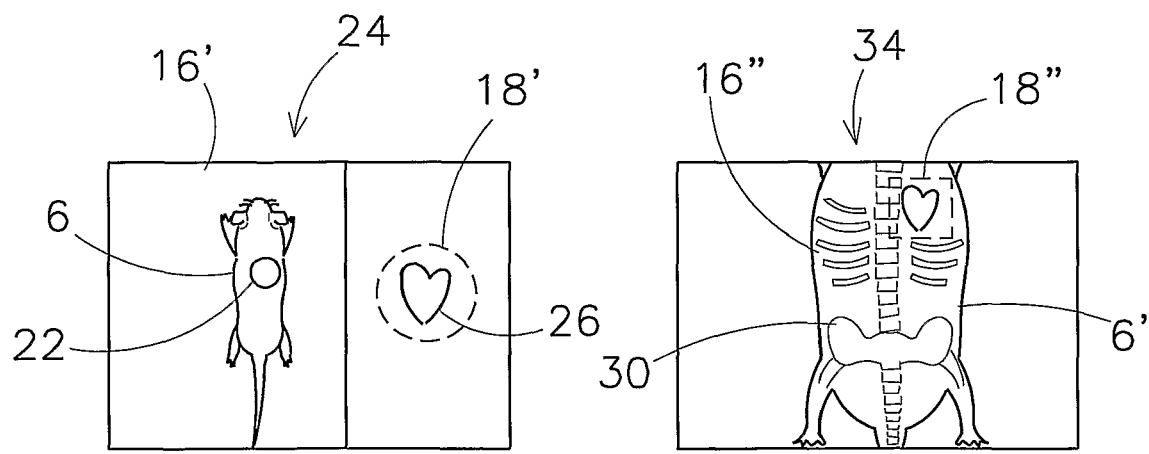
FIGS. 2a and 2b each show a screen with a first and a second image.

FIGS. 2a and 2b diagrammatically show two screens, indicative of ways of displaying by means of the device and the method according the invention. Although the screens are shown separately here, it is stressed here that the images to be displayed thereon may also be shown on one screen, such as sequentially or even at the same time.

FIG. 2a shows a screen 24 with a second image 16' to the left, showing a test animal 6', and furthermore, with the dashed line there is indicated at 22 where a first image 18' is located. To the right on the screen 24, that first image 18' is shown, with a diagrammatic heart 26.

The second image 16' is e.g. an optical image of, in this case, a plan view of the test animal 6'. The dashed line 22 indicates the position of the focus volume of the gamma camera (not shown), that makes the first image 18'. The operating person may scan through the test animal 6' in a very dedicated fashion, by e.g. selecting a desired part of the test animal 6' by means of a mouse or the like, of the control device (not shown). The object holder displacement device (not shown) then directs the object holder with the test animal 6' to the corresponding position. This offers an eminent possibility to the operator, such as a researcher, to examine an interesting area, but especially to situate it with respect to its surrounding.

In FIG. 2a, the test animal 6' is shown in a plan view only, and thus there may be shown two dimensions of it, in other words, two co-ordinates of box 22. If two or more first images are made of the test animal 6', there may also be made a spatial reconstruction, either by projecting a 3D projection, that is e.g. rotatable, on the screen 24, or by e.g. displaying the two or more images next to each other on the screen 24. Then, e.g. this concerns a plan view and a left or right side elevational view. In all cases, a more precise localization of the focus field for the second image 18' is then possible. Selecting may then be carried out by selecting a desired part in the image by means of a mouse, or e.g. by framing that desired part by means of lines or a rectangle or the like, preferably in a plurality of images, such that a three dimensional selection or framing is brought about.

In FIG. 2b there is shown a screen 34 with the second image 16" as well as a first image 18" projected therein or on top of it. Again, a diagrammatic heart is indicated therein, and now with respect to an anatomical atlas of the skeleton 30 of the test animal 6'.

In this embodiment, the first image, i.e. the gamma camera image, is thus imaged over the second image of the test animal (or the human being), and here even with a projected anatomical atlas. This provides optimum possibilities to show a gamma image in its relation to its surrounding in the body. In this case too, it is possible to make a spatial, 3D reconstruction of the test animal, both for the first image and for the second image, and their spatial relationship. Then it is necessary to have both a plurality of gamma cameras and a plurality of other, such as optical or CT detectors, on the basis of which the reconstruction may be made.

In the example shown, the first and/or the second image may be rendered in false colours, e.g. to indicate a certain quantity. It is also possible to display the first image 18" magnified with respect to the second image 16", in order to stress details. The skeleton 30 is depicted in the image of the test animal 6'. Herein, use is made of known anatomical atlases, that are e.g. stored in a data file in the control device. By selecting the desired type of atlas, associated with the type of test animal, and by "fitting" it to the dimensions of the test animal and a possibly selected image scale, the atlas may be displayed in the right proportions. Although deviations of the test animal with respect to the atlas are possible, yet a very good starting position for navigation is provided. It is also possible to make an X-ray, CT scan or the like, as an alternative detector, such that the exact structure of the skeleton, or another part of the test object, may be made visible.

It is also visible in FIG. 2b that a smaller part of the test animal 6' is visible than in FIG. 2a. This may be achieved with a zooming function or change of distance for the additional detector and so on.

Figure 3:
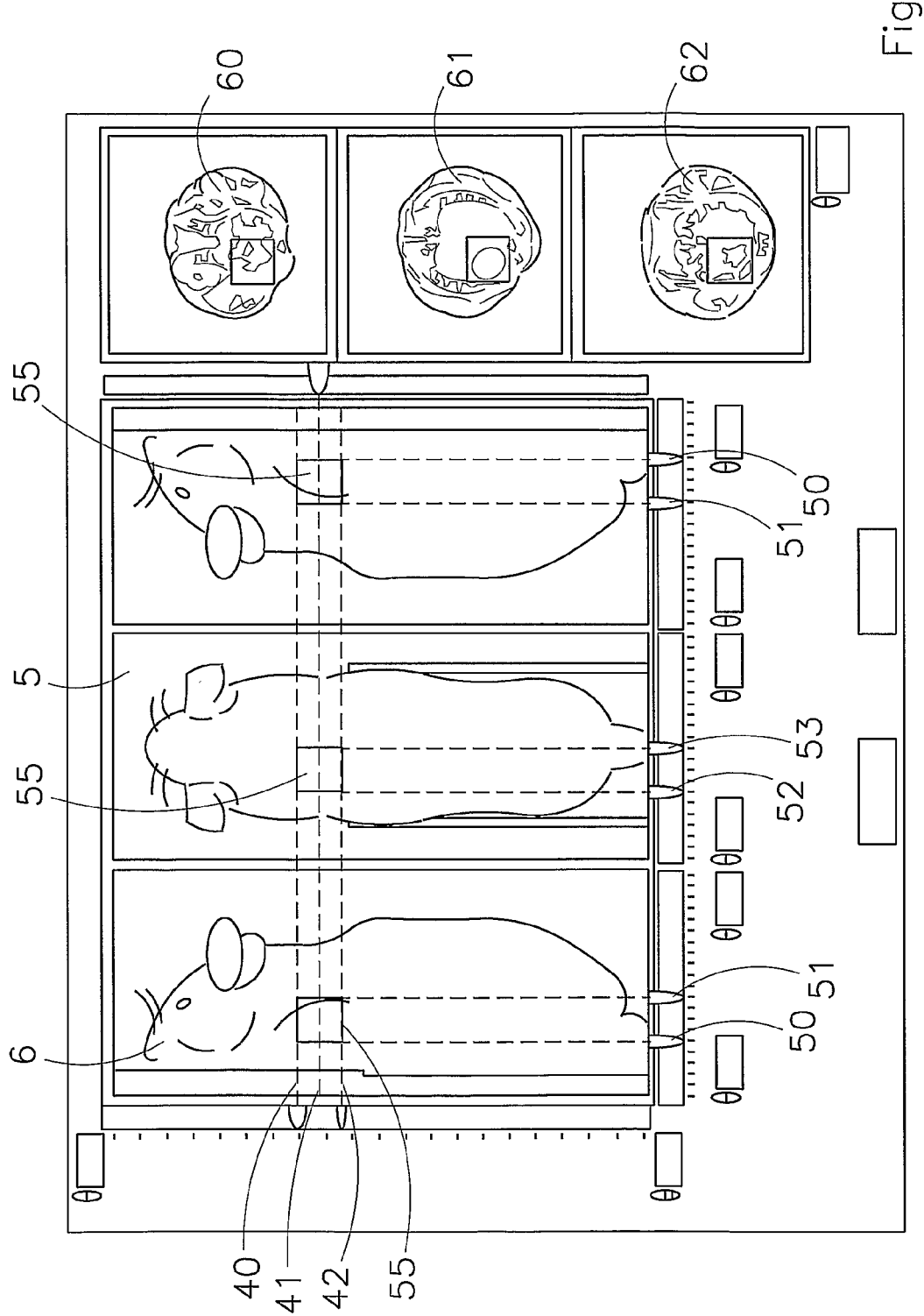
FIG. 3 shows a screen of an advantageous embodiment.

FIG. 3 shows a screen of an advantageous embodiment. In this screen, there are shown three optical images 'Left', 'Top' and 'Right', of a mouse 6 on an object holder 5, that may be made with optical cameras 10 from FIG. 1. In the three images, a limited area 55 has been indicated by means of lines 40 and 42, 50 and 51, and 52 and 53, respectively. In the right part of the screen, first through third cross-sectional views 60, 61, 62 are shown. It can be seen that the object holder 5 is at least optically transparent, so that if desired, a fourth camera with a corresponding image may be added. The three cameras and images used here show an image of the mouse 6 from three sides, from the left, from the top and from the right.

In the mouse 6, an area 55 has been indicated, that indicates the desired examination area. This area is delimited by lines (actually planes) 40 and 42, perpendicular to the longitudinal direction of the mouse 6, and by four lines 50-53 parallel to the longitudinal direction of the mouse 6. Herein, the lines in the 'Right' image are in principle a mirror image of the lines 50 and 51 in the 'Left' image.

Here, the area 55 is a cube, but it can have any desired shape. The dimensions and position of the area 55 may be set by displacing the lines 40, 42 and 50-53. This may e.g. be done based on the size settings at the bottom of the images. Herein, use may be made of a number of tools. For example, an anatomical atlas of the mouse, or a different mouse such as an average mouse, may be projected into the three images 'Left', 'Top' and 'Right'. In this case however, there are shown three cross-sectional images ("slices") 60, 61 and 62 of a 3D reconstruction from an MRI scan, that was made before or that originates from a general mouse and has been brought in register with this mouse 6. Herein, the positions of the cross-sections 60, 61 and 62 are coupled with the positions of the lines (actually planes) 40, and 41 and 42, respectively, in the images 'Left', 'Top' and 'Right'. This offers e.g. the following advantageous possibility.

A user displaces e.g. line 40 through the mouse 6, by means of the cursor. On doing that, the displayed image 60 will change according to the position in the mouse 6. The user then selects e.g. the top edge of an area to be examined, e.g. the top edge of a heart or other organ (system). Accordingly, he can displace the line 42 with the cursor, such that this indicates the lower edge. Again, the corresponding cross-sectional image 62 to the right offers visual feedback. If desired, line 41 may also be used, e.g. if the area to be examined surrounds a small desired area, such as a small organ, with a certain margin. This margin may then be set as desired, such as symmetrically around the small area.

After setting these lines 40, 42, 50-53 and possibly 41, the desired area to be examined is delimited and the actual gamma detection may be performed. The mouse 6 is displaced in the detection device, along a known path, such that the correspondence between gamma detection image and the optical images made in advance is actually brought about. Herein, it is possible that the focus volume is smaller than the desired area. Then, the focus volume needs to be scanned through the area, preferably automatically. If the focus volume is larger than the area to be examined, it suffices of course to have both areas overlap sufficiently.

The strength of the invention is again shown with this embodiment, although this also shows in many described alternative embodiments. Simple optical cameras provide, with their images, a means for localization in the object, here the mouse 6. In these images, an area to be examined may be delimited, whether or not with extra information, such as in anatomical atlas projected therein or displayed next to it. Subsequently, a gamma detection image is made of the delimited area to be examined.

Since, as can be clearly seen e.g. in this FIG. 3, the area to be examined will be a relatively small part of the object, it will be clear that a lot of scanning time may be saved with the device and method according to the invention. In particular the rough gamma prescan, that is often applied but of course only provides a rough image, may thus be omitted. The good coupling between the gamma detection image and e.g. the optical images of the object allow reliable and user-friendly interpretation of that gamma detection image.

FIG. 4 shows a diagrammatical cross-section of an embodiment of the detection device according to a further aspect of the invention. Herein, 101 denotes a frame with a central detection space 102. Gamma detector surfaces have been denoted by 103, while an X-ray detector 104 and an X-ray source 105, with an arm 106, have been mounted on a gantry 107.

A collimator 108 has pinholes 109, while a test animal 111 is lying on an object holder 110.

Finally, 112 denote two optical cameras.

The frame 101 is triangular here, but it can also be cylindrical or polygonal. The detection space 102 is mostly cylindrical, with a longitudinal direction that is perpendicular to the plane of the Figure.

The gamma detector surfaces 103 comprise e.g. gamma scintillation crystals or similar gamma detectors known in the art. Preferably, they are position sensitive.

The X-ray detector 104 e.g. comprises X-ray scintillation crystals, and also is preferably a position sensitive detector. Generally, it holds that the embodiments shown in the Figures are restricted to X-ray sources and X-ray detectors. This aspect of the invention, however, also comprises other transmissive radiation, and sources and detectors thereof, such as gamma and synchrotron radiation. In each case, these types of radiation should hence also be included when reading "X-ray".

The X-ray source 105 may also, in principle, be any known X-ray source, preferably having sufficiently small dimensions to allow positioning in a device according to this aspect of the invention, and more preferably forming a point source. The X-ray source may again also be a different radiation source, such as a gamma source, again preferably as a point source. The energy of such an external gamma source is preferably different from, and more preferably smaller than, that of the gamma tracer(s) brought into the object to be examined.

The X-ray source 105 shown is optionally displaceable from the "parking position" shown in FIG. 4 to a working position closer to the detection space 102. Thereto, arm 106 is e.g. telescopically extendible and retractable on gantry 107. This gantry 107, together with X-ray source 105 and X-ray detector 104, is rotatable around the object in the detection space 102, to thereby be able to make an X-ray CT scan. It can be seen that the X-ray source 105 in the "parking position" hardly or not disturbs the gamma measurements on the gamma detection surfaces 103. Furthermore, the gantry 107 comprises two optical cameras 112, e.g. of the webcam type. These may be used to make optical images, e.g. for optical tomography. For the purpose of these optical images, this tomography, respectively, but of course also for the X-ray CT scan, the object 111 on the object holder 110 may be displaceable, at least in a direction along the longitudinal direction of the detection space 102. This displacement may be e.g. stepwise or uniform, for a circular acquisition or a helical scan acquisition, respectively, both for the optical CT scan and for the transmission CT scan. For the purpose of the gamma camera, which is in principle constituted by the gamma detection surfaces and a processing unit not shown here, there is further provided a collimator 108, with pinholes 109. The pinholes 109 of this collimator 108 known per se are all directed with their main transmission direction to a focus volume within the detection space 102. Thus, a very good resolution is obtained, with a still relatively high sensitivity. Note that such a collimator 108 is not necessary, e.g. in a PET scanner. The collimator may, to that end, be retractable from the detection space 102.

Hereafter, there will be elucidated how scanning with SPECT/PET as well as CT can be performed with the device according to the invention.

FIG. 5 shows a cross-sectional side elevational view of an embodiment of the device according to this aspect of the invention. Besides similar parts as in FIG. 4, which will be indicated in each case in the Figures with the same reference numerals, the embodiment of the device of FIG. 5 furthermore comprise a pinhole blocking tube 120 with holes 121, and which is e.g. displaceable in the direction of the arrow. Note that only one half of this tube 120 has been drawn. Incidentally, it is also possible to provide not a tube but e.g. a tube part or sheet, preferably opposite the X-ray source 105, and also for the tube 120 or the alternative tube part or sheet to form one integral unit with the gantry. Furthermore, in FIG. 5, the X-ray detector 104, as well as the X-ray source 105, is now located at the level of the collimator 108. Incidentally, it will often occur in practice that the detector 104 is displaced a bit outwardly with respect to the collimator 108, since the detector 104 is often relatively bulky, at least provided with bulky peripheral equipment.

In use, for making an X-ray CT scan, the device will turn the gantry 107 with the X-ray source 105 and the detector 104, if desired at the same time displacing the test animal 111 through the detection space 102 in longitudinal direction. Herein, the pinholes 109 are preferably blocked. In FIG. 5, a demarcation line between the gantry 107 and the collimator 108 is drawn. However, it is also possible to make these parts as one unit.

To make a gamma scan, the pinhole blocking tube 120 will release the pinholes 109 again by aligning the holes 121 therewith.

Subsequently, the gamma radiation, which originates from gamma sources within the test animal 111, will be detected via the pinholes 109, on the gamma detection surfaces 103. Here, they are separate surfaces, e.g. separate scintillation crystals. It is also possible to provide one big detection surface, which could then e.g. be framed onto the various pinholes by means of the framing device. In this device, the various pinholes are directed to a focus area. See to that end the main transmission directions, indicated by means of dashed lines, of two pinholes. The X-ray CT scanner, too, may be aligned with respect to this focus area, in the perpendicular bisector plane indicated with the dot-dashed line. Thus, a gamma image and an X-ray image may be made simultaneously, without displacing the test animal with respect to the gamma and/or X-ray detector surfaces. This offers great advantages as to ease of use and accuracy.

FIG. 6 shows, in a diagrammatic cross-section, an alternative embodiment.

Herein, the gamma detector surfaces 103 have been applied onto a carrier body 113. Just like the collimator 108, this carrier body 113 is built up of two parts, that are displaceable apart in the direction of the arrow. Thus, room is made through which the X-ray source 105 and the X-ray detector 104 can make an image. For a gamma scan, the two parts of the carrier body 113 with the gamma detector surfaces 103, as well as those of the collimator, are in each case abutted again. This embodiment is e.g. favourable if a high resolution SPECT scan needs to be made, such as with the U-SPECT III, see also the article by M. Rentmeester et al., Optimizing multi-pinhole SPECT geometries using an analytical model (in press 2007). For in that case the pinholes and also the gamma detectors are positioned very close to the test animal, due to which there is often no room within the collimator for an X-ray source with sufficient intensity.

FIG. 7 shows a side elevational view in diagrammatical cross-section of an embodiment of the central part of the device according to the invention, with the X-ray CT scanner. Herein, the X-ray source 105 and the X-ray detector 104 are arranged in a metal disc 122 with an opening that fits to the detection space. The disc is driven by a drive wheel 123 with a drive belt 124, and is supported on two bearing wheels 125.

In fact, the disc 122 here forms a kind of gantry with an opening. In use, the disc 122 will rotate, to thereby be able to collect the required angular information. I desired, the animal 111 may be displaced through the opening of the disc 122 stepwise or uniformly. FIG. 8 shows a perspective view of the embodiment in FIG. 7. Herein, the X-ray source 105 and the X-ray detector 104 are indicated in the disc 122. Moreover, two tube parts 126 are depicted, that connect to an (optional) collimator. Note that the X-ray CT scan set-up shown here gives a very narrow rectangular image, with a similarly narrow beam. In case that beam is more narrow than the test animal 111, then a displacement of the test animal 111 may be applied for the purpose of an X-ray image. Although such an arrangement need not give a higher resolution by itself, the detector may however remain smaller, which makes reading it out faster, and it can also be cheaper.

The tube parts 126 may also serve as pinhole blocking tubes. Thereto, they could be provided with holes (not shown). In an embodiment, these holes in the tube parts 126 could release the pinholes, e.g. when rotating the whole. Then it is possible to release the pinholes, during rotation, only when the X-ray source is switched on. The latter should then be operated in pulsed mode. Alternatively, and advantageously, the tube parts, together with the disc 122 with the X-ray CT set-up or not, may be displaced over such a distance in the z-direction, that the holes that release the pinholes in the non-displaced position, are now positioned between the pinholes. Thus, the pinholes are always blocked when the disc 122 is displaced and the X-ray source 105 is switched on.

The invention has many advantages, of which it is stressed here that, in the first aspect of the invention, the mapping of the object prior to the gamma detection offers the possibility to scan that object efficiently and quickly. By performing this mapping in a separate space, and with detectors other than gamma detectors, it is easy to select the best suited imaging. The images takes for the mapping, such as optical images or the like, may, if desired, be displayed in the form of a spatial reconstruction. Furthermore, e.g. an anatomical atlas may be used or projected. The operating person may navigate in all these images, that is to say, indicate an area to be examined. The images recorded with the gamma detection may subsequently be displayed either separately, or in the images or reconstructions shown, in order to further facilitate efficient navigation and interpretation of the images thereby.

The exemplary embodiments mentioned and described are meant to elucidate the invention, not to delimit the scope of protection. The skilled person will easily be able to carry out modifications and changes that fall within the scope of the invention, the scope of protection of which is determined with the attached claims.

The invention claimed is:

1. A detection device, comprising:
   a first detector;
   a second detector;
   an object holder;
   an object holder displacement device;
   a control device; and
   a selection device,
   wherein the first detector comprises a gamma detection space with a gamma camera having a first field-of-view that is located in the gamma detection space,
   the second detector comprises an additional camera that is substantially sensitive to radiation that differs from gamma radiation, and having a second field-of-view outside the gamma detection space,
   the control device comprises a screen, wherein the control device and the screen are configured to make a second image taken by the second detector and display the second image prior to taking and displaying a first image by the first detector, and
   the object holder displacement device is arranged to displace the object holder along a path that is controllable by the control device, and
   wherein the selection device is configured to select a part of an object to be examined to be detected by the first detector based on the second image prior to making the first image of the part of the object.

2. The detection device according to claim 1, comprising a plurality of additional detectors.

3. The detection device according to claim 2, wherein the additional detectors comprise at least one of an optical camera, an MRI scanner, a CT scanner or an X-ray camera.

4. The detection device according to claim 1, wherein the second field-of-view comprises the complete object to be examined, in particular the complete part to be examined of the object.

5. The detection device according to claim 1, wherein the control device is arranged to display the first and second image next to each other on the screen.

6. The detection device according to claim 1, wherein the control device is arranged to project the first image in, or over, the second image, or to project the second image over the first image.

7. The detection device according to claim 5, wherein the control device is switchable between displaying next to each other and displaying on top of each other.

8. The detection device according to claim 1, wherein the control device is arranged to project an anatomical image or atlas of at least a part of the object over the first and/or second image.

9. The detection device according to claim 8, wherein the control device is arranged to adapt a rendering of at least one of the first and second image and the anatomical atlas to the rendering of the other of the first and second image and the anatomical atlas.

10. The detection device according to claim 1, wherein the object holder displacement device is arranged to displace the object holder in at least two dimensions.

11. The detection device according to claim 1, wherein the object holder displacement device is arranged to displace the object holder in three dimensions.

12. The detection device according to claim 1, further comprising a plurality of gamma cameras.

13. The detection device according to claim 12, wherein the respective fields-of-view of the gamma cameras overlap only partly, and define a focus volume.

14. The detection device according to claim 13, wherein the control device is arranged to make and display a spatial reconstruction from respective first images of the focus volume of the gamma camera.

15. The detection device according to claim 1, comprising a plurality of additional cameras, wherein the control device and the screen are arranged to display of either a plurality of second images from the plurality of additional cameras, or a plurality of views, that are desired projections of a three-dimensional reconstruction of the object based on a plurality of second images.

16. The detection device according to claim 15, wherein the selection device is arranged for selecting a part to be examined of the object on the object holder in a plurality of second images, in a plurality of views of the object, respectively.

17. The detection device according to claim 1, wherein the control device is arranged for selecting a part of an anatomical image, in particular an organ, or organ group, a body part or tissue of a test animal.

18. The detection device according to claim 1, wherein the control device is arranged to automatically turn a part that is selected in an anatomical atlas into the to be examined part of the object.

19. The detection device according to claim 1, further being arranged to displace the object holder in a such a way that, after displacement, the part to be examined overlaps with a focus volume.

20. A method of making a gamma detection image, using a detection device which comprises:
a first detector;
a second detector;
an object holder;
an object holder displacement device;
a control device; and
a selection device,
wherein the first detector comprises a gamma detection space with a gamma camera having a first field-of-view that is located in the gamma detection space,
the second detector comprises an additional camera that is substantially sensitive to radiation that differs from gamma radiation, and having a second field-of-view outside the gamma detection space,
the control device comprises a screen, wherein the control device and the screen are configured to display a second image made by the second detector prior to making a first image by the first detector, and
the displacement device is arranged to displace the object holder along a path that is controllable by the control device, and
wherein the selection device is configured to select a part of an object to be examined to be detected by the first detector based on the second image prior to making the first image of the part of the object,
wherein the method comprises the steps of:
positioning an object on the object holder,
making and displaying a second image with an additional detector,
selecting a part of the object to be examined based on the displayed second image,
a path along which the object is to be displaced, and
making and displaying a first image, being the gamma detection image.

21. The method according to claim 20, wherein at least one of the first and second image are displayed as a two-dimensional image, a three-dimensional spatial reconstruction or a cross-section (slice) thereof.

22. The method according to claim 20, wherein the first and second image are displayed on the screen simultaneously.

23. The method according to claim 20, wherein the first image is projected into the second image.

24. The method according to claim 20, wherein an anatomical image or atlas is projected in the second image and brought in register therewith.

25. The method according to claim 24, wherein displaying the second image is ended.

26. The method according to claim 20, wherein determining of the path takes place by the control device automatically, after a user has selected a part of the object to be examined.

27. The method according to claim 20, wherein the steps of selecting, determining and making and displaying a first image are repeated.

* * * * *